United States Patent [19]

Porter

[11] 4,175,119
[45] Nov. 20, 1979

[54] COMPOSITION AND METHOD TO PREVENT ACCIDENTAL AND INTENTIONAL OVERDOSAGE WITH PSYCHOACTIVE DRUGS

[76] Inventor: Garry L. Porter, 507 N. Volutsia, Wichita, Kans. 67214

[21] Appl. No.: 868,607

[22] Filed: Jan. 11, 1978

[51] Int. Cl.² .................... A61K 9/30; A61K 31/00
[52] U.S. Cl. .................................................. 424/10
[58] Field of Search ..................................... 424/10

[56] References Cited

U.S. PATENT DOCUMENTS 2,957,804  10/1960  Shuyler .................................. 424/7

OTHER PUBLICATIONS

Franklin, "Built-in Lifeguard", Time, Aug. 2, 1948, p. 32, (Ipecac Emetic in Sleeping Tablets, Rat Paste and Other Poisons).
Kefauver, Washington, D.C., Sunday Star This Week Magazine, Mar. 20, 1949, pp. 4, 5, 22, "Let's Stop Sleeping-Pill Suicides."
Miskimon Virginia Medical Monthly: 119–122(1950), "A Method for the Prevention of Suicidal Deaths Caused by Barbituric Acid Derivatives."
Anon J.A.M.A. 146, (10):977 Jul. 7, 1951, "Sleeping Pills Containing an Emetic," Merck Index 9th Ed., 1976, Merck & Co., #1931, #3508–11, Cephaeline, #4926 Emetine, HCL, #7715 Ipecac, Psychotrine.

*Primary Examiner*—Shep K. Rose
*Attorney, Agent, or Firm*—John H. Widdowson

[57] ABSTRACT

A composition and method of inducing emesis to preclude death from accidental or intentional overdosage of a therapeutic composition. The surface of the therapeutic composition is coated with an emetic chemical of such quantity that if the therapeutic composition is consumed in moderation or in accordance with the prescription, no emesis occurs; but if consumed excessively and not in accordance with the prescription, emesis results to render the therapeutic composition harmless and precludes death or serious illness.

53 Claims, No Drawings

COMPOSITION AND METHOD TO PREVENT ACCIDENTAL AND INTENTIONAL OVERDOSAGE WITH PSYCHOACTIVE DRUGS

BACKGROUND OF THE INVENTION

1. Field of the Invention

This invention is related to a medical composition. More specifically, this invention provides for a therapeutic composition being coated with an emetic envelope to prevent accidental and intentional overdosage.

2. Description of the Prior Art

Since the middle of this century, the world has experienced an explosion of thousands of new types of medications. Accompanying this emerging chemical society has been the common occurrence of the overdose. Many of these drugs are either intentionally psychoactive (e.g. psychotropics, sedatives, hypnotics, analgesics, etc.) or are so as a side effect (e.g. antihistamines, antiseizure medications, etc.).

There are hundreds of thousands of accidental and intentional self-destructive incidents a year. These range from small children ingesting medication left available to them, to automatic pill taking in clouded consciousness states, to impulsive ingestion, to calculated suicide attempts. Many people die each year, whether from intention or miscalculation.

U.S. Pat. No. 3,260,646, patented July 12, 1966, teaches the addition of nicotinic or tolazoline, hydrochloride or beta pyridil carbinol tartrate or isoxsuprine to a therapeutic composition to cause severe peripheral vasodilation as evidenced by substantial flushing. U.S. Pat. No. 2,967,131, patented Jan. 3, 1961, teaches utilization of fluoride ions to produce emesis. These patents, nor any other prior art, teach the improved method and composition to prevent overdosage which I have invented.

SUMMARY OF THE INVENTION

It is therefore an object of this invention to provide a composition and method to prevent accidental and intentional overdosage with psychoactive drugs or any other therapeutic compositions.

Still other objects will be apparent to those skilled in the art from the following description of this invention.

The foregoing objects are achieved according to the practice of this invention. Broadly, this invention comprises a therapeutic composition adapted to prevent drug overdosage and adapted for oral administration in addition to therapeutic ingredients having psychoactive characteristics including a coating on the surface of the therapeutic composition. The coating has between about 0.25 and 2.0 mg. of an emetic chemical selected from the group consisting of methyl cephaeline, cephaeline, emetine hydrochloride, psychotrine, O-methylpsychotrine, emetamine, ipecamine, hydro-ipecamine, ipecacuanhic acid, and mixtures thereof. This invention also broadly comprises a method of inducing emesis to preclude death to a being from accidental or intentional overdosage of a therapeutic composition, which is normally of the type which if ingested by prescription is safe, but if excessively ingested is lethal. The method includes the steps of coating the surface of the therapeutic composition with the emetic chemical; controlling the quantity of the emetic chemical coated on the surface of the therapeutic composition such that no emesis ensues if normal prescription directions are followed or if no overdosage occurs; ingesting excessive quantities by the being of the coated therapeutic composition; and, producing emesis in order to preclude death or serious illness in the being.

Thus, by the practice of this invention, there is provided a method and composition of matter to prevent accidental and intentional overdosage of a therapeutic composition which is normally, but doesn't have to be, of the type which is ingested by prescription is safe, but if excessively ingested, is lethal.

DETAILED DESCRIPTION OF THE INVENTION

This invention includes coating the surface of a therapeutic composition with an emetic chemical selected from the group consisting of methyl cephaeline ($C_{28}H_{38}O_4H_2$), cephaeline ($C_{28}H_{38}O_4H_2$), emetine hydrochloride ($C_{30}H_{44}O_4N_2 2HCR$), psychotrine ($C_{28}H_{36}O_4N_2$), O-methylpsychotrine, emetamine, ipecamine, hydro-ipecamine, ipecacunhic acid, and mixtures thereof. Preferably, the emetic chemical has a major proportion of methyl cephaeline and cephaeline, and a minor proportion of psychotrine, O-methylpsychotrine and emetamine. In a preferred embodiment of the invention, the emetic chemical comprises between about 40% wt. and 85% wt. of methyl cephaeline, between about 10% wt. and 40% wt. of cephaeline, between about 2% wt. and 12% wt. of psychotrine, between about 1% wt. and 6% wt. of O-methylpsychotrine, and between about 1% wt. and 6% wt. of emetamine. Additional embodiments of the invention provide for the emetic chemical additionally having between about 1% wt. and 6% wt. of ipecamine between about 1% wt. and 6% wt. of hydro-ipecamine, between about 1% wt. and 6% wt. of ipecacuanhic acid, and between about 1% wt. and 6% wt. of emetine hydrochloride.

The coating preferably has between about 0.25 mg. and 2.0 mg. of the emetic chemical. More preferably, the coating includes between about 0.25 and 2.0 mg. of the emetic chemical. The quantity of the emetic chemical on the surface of the theraputic composition should be controlled such that the dosage per coating per therapeutic composition would be so small as to be unnoticeable by itself, but such as to have an accumulation of a total dosage of at least 21 mg. of the emetic chemical if taken in any significant number would produce vomiting in 90% to 95% of the adult population in 10 to 15 minutes. The concentration per coating would be flexible to account for differing $MLD_{50}$ and therapeutically effective levels of dosage prescription. It has been discovered that the coating of the emetic chemical should be controlled such as not to exceed 2.0 mg. per therapeutic composition. It has also been discovered that the emetic chemical of this invention depending on the constituents and concentration of constituents, is sensitive to lighting and should therefore be enveloped with an opaque coating means, well known to those skilled in the art.

It is important in this invention that the therapeutic composition be enveloped or coated with the emetic chemical instead of commingling or admixing the emetic chemical with the therapeutic composition. The underlying principle would be that if a being accumulated sufficient tablets or capsules in the stomach, the first active ingredient to be dissolved or touch the gastric lining would be the contents of the protective envelope of the emetic chemical and emesis would occur before any significant amount of therapeutic composition from the tablet or capsule could be absorbed. The mechanism of emesis production is primarily local in the stomach. Many of the psychoactive drugs inhibit emesis, an added reason for having the emetic chemical in a surface or first contact position. Coating, well known to those skilled in the art (e.g. pan coating, air-suspension coating, compression coating, etc.), controls the rate and site of the emetic chemical release.

The emetic chemical of this invention has been found to be much more effective than other emetics such as apomorphine, ammonium carbonate, cupric sulfate, tartar emetic, zinc sulfate, blacks mustard, sanguinaria, copper sulfate, eucalyptole, eucalyptus oil, glycynhiza, guaiacol, lobelia, potassium iodide, senega terebene, terpin hydrate, thyme, etc.

The therapeutic composition may come in any size tablet, capsule, etc., such as 0.1, 0.5, 1, 5, 10, 25, 30, 50, 75, 100, 150, 200, 300, etc., mg. The therapeutic compositions may be neuroleptic drugs, e.g., there are eight classes: Phenothiazine (chlorpromazine, thioridiazine, trifluoperazine, fluphenazine, promazine, triflupromazine, mesoridazine, piperacetazine, acetophenazine, butaperazine, carphenazine, perphenazine, prochlorperazine, thiopropazine, thioproperazine, etc.), butyrophenones (haloperidol, triperidal, etc.), rauwolfia derivatives (Reserpine (rauwolfia), rauwolfia serpintina, etc.), benzoquinolizines (tetrabinazine, etc.), phenylpiperazine (oxypertine, etc.), acridan, indolic derivatives (molindone, etc.), and loxapine. The therapeutic composition may also be any of the anxiolytics/minor tranquilizers such as benzodiazepines (diazepam oxazepam, chlordiazepoxide, Librax (chlordiazepoxide and clidinium) etc.), diphenylmethanes, hydroxyzine (Atarax (hydroxyzine), Vistarial (hydroxyzine pamoate), etc.), chlormezanone, meprobamate; or sedative-hypnotics, such as barbiturates (secobarbital sodium, phenobarbital, amobarbital, pentobarbital, Carbital (pentobarbital and carbomel), mephobarbital, Tuinal (secobarbital and amobarbital), butabarbital, etc.), glutethimide, fluazepam, methprylon, ethchlorynol, promethazine, chloralhydrate, methaqualone, etc; or lithium carbonate, methylphenidate, Etrafon (perphenazine and amitriptylline), Triavil (perphenazine and amitriptylline); or anticonvulsants such as phenytoin sodium, mephenytoin, paramethadione, trimethadione, etc.; or an antiparkinsonian drug such as trihexyphenidyl, procyclidine HCI, benztropine, etc.; or antidepressants such as tricyclics (amitriptyline, imipramine HCI, nortriplyline HCI, desipramine HCI, etc.), doxepin, MAO inhibitors (tranylcypromine, isocarboxazid, nialamid, phenelzine, etc.) protrystyline HCI; or, anorexics such as amphetamines (amphetamine sulfate, dextro amphetamine, levo amphetamine, methamphetamine HIC), nonamphetamines (phentermine resin, diethylproprion, phenmetazine HCI, mazindol, etc.) etc; or analgesics such as narcotics (dolophin meperedine, oxycodone, hydromorphone HCI, codine, etc.), pentazocine HCI and derivative, acetylsalicylic acid, Fiorinal (butalbital, phenacetin, ASA, and caffiene), propexyphene, propexyphene napsylate, Coriciden (chlorpheniramine and ASA), acetaminophen, etc.; or muscle relaxants such as orphenadrine citrate, chlorzoxazone, carisoprodol, methocarbomal, phenylbutazine; or any of the antihistamines such as dimenhydrinate, pseudoephedrine, trimeprazine, gusarfenesin, Tus-Ornade (chlorpheniramine, phenylpropanolamine and caramiphen), Ornade (chlorpheniramine and phenylpropanolamine), promethazine HCI, phenylpropavolamine, pheniramine, pyrilamine, pyribenzamine, trimethobenzamide, diphenhydramine, chlorpheniramine, etc.; or any medicinal composition.

EXAMPLE I

Take any of the therapeutic compositions mentioned in the previous paragraph; coat the surface of the therapeutic compositions with about 0.25 mg. of an emetic chemical having a major proportion of methyl cephaeline and cephaeline and a minor proportion of psychotrine, O-methylpsychotrine and emetamine; continuously, orally administer the coated therapeutic composition to a human being (insuring emergency emetic means are readily available); and find that the human being will vomit the coated therapeutic composition after about 10 minutes and when the accumulation of the emetic chemical dosage is 21 mg. or greater.

EXAMPLE II

Repeat Example I, but coat the surface of the therapeutic composition with about 2.0 mg of the emetic chemical and find similar results.

EXAMPLE III

Repeat Example II with the emetic chemical comprising about 40% wt. of methyl cephaeline, about 40% wt. of cephaeline, about 12% wt. of psychotrine, about 4% wt. O-methylpsychotrine, and about 4% wt. emetamine, and insuring that the emetic chemical on each therapeutic composition does not exceed 2 mg. Find similar results.

EXAMPLE IV

Repeat Example II with the emetic chemical comprising about 60% wt. of methyl cephaeline, about 30% wt. of cephaeline, about 6% wt. of psychortine, about 2% wt. of O-methylpsychotrine, about 2% wt. of emetamine; and find similar results.

EXAMPLE V

Repeat Example IV with the emetic chemical comprising about 56% wt. of methyl cephaeline, about 26% wt. of cephaeline, about 6% wt. of psychotrine, about 2% wt. of O-methylpsychotrine, about 2% wt. of emetamine, about 4% wt. ipecamine, about 4% wt. of hydro-ipecamine, and find similar results.

EXAMPLE VI

Repeat Example V with the emetic chemical comprising about 50% wt. of methyl cephaeline, about 20% wt. of cephaeline, about 12% wt. of psychotrine, about 2% wt. of O-methylpsychotrine, about 2% wt. of emetamine, about 4% wt. of ipecamine, about 4% wt. of hydroipecamine, about 2% wt. of ipecacunhic acid, about 4% wt. of emetine hydrochloride, and find similar results.

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth.

I claim:

1. A method of inducing emesis to preclude death from accidental or intentional overdosage of a therapeutic composition, which is normally of the type which if ingested by prescription is safe, but if excessively ingested is lethal, comprising the steps of:
  a. coating the surface of the therapeutic composition with between about 0.25 and 2.0 mg. of an emetic chemical comprising a major proportion of methyl cephaeline and cephaeline and a minor proportion of psychotrine, O-methylpsychotrine, and emetamine;
  b. controlling the quantity of said emetic chemical coated on the surface of the therapeutic composition such that no emesis ensues if normal prescription directions are followed or if no overdosage occurs;
  c. ingesting excessive quantities by a being of said therapeutic composition of step (b), said excessive quantities comprising an accumulation of a total dosage of at least 21 mg. of the emetic chemical; and,
  d. emesis by said being of the ingested excessive quantities of coated therapeutic composition of step (c) in order to render the therapeutic compositions harmless and preclude death or serious illness to said being.

2. The method of claim 1 additionally including coating said therapeutic composition with an opaque means after step (b).

3. The method of claim 1 wherein said therapeutic composition is a muscle relaxant.

4. The method of claim 1 wherein said therapeutic composition is an antihistamine.

5. The method of claim 1 wherein said therapeutic composition is selected from the group consisting of perphenazine and amitriptylline, perphenazine and amitriptylline, and mixtures thereof.

6. The method of claim 1 wherein said emetic chemical comprises between about 40% wt. and 85% wt. of methyl cephaeline, between about 10% wt. and 40% wt. of cephaeline, between about 2% wt. and 12% wt. of psychotrine, between about 1% wt. and 6% wt. of O-methylpsychotrine, and between about 1% wt. of 6% wt. of emetamine.

7. The method of claim 6 wherein said controlling step (d) comprises insuring that said emetic chemical does not exceed 2 mg per therapeutic composition.

8. The method of claim 7 wherein said emetic chemical includes between about 1% wt. and 6% wt. of ipecamine and between about 1% wt. and 6% wt. of hydroipecamine.

9. The method of claim 8 wherein said emetic chemical includes between about 1% wt. and 6% wt. of ipecacuanhic acid.

10. The methof of claim 9 wherein said emetic chemical comprises between about 1% wt. and 6% wt. of emetine hydrochloride.

11. The method of claim 1 wherein said therapeutic composition is a neuroleptic drug.

12. The method of claim 1 wherein said therapeutic composition is an anxiolytic/minor tranquilizer.

13. The method of claim 1 wherein said therapeutic composition is a sedative-hypnotic.

14. The method of claim 1 wherein said therapeutic composition is lithium carbonate.

15. The method of claim 1 wherein said therapeutic composition is methyl-phenidate.

16. The method of claim 1 wherein said therapeutic composition is an anticonvulsant.

17. The method of claim 1 wherein said therapeutic composition is an antiparkinsonian drug.

18. The method of claim 1 wherein said therapeutic composition is an antidepressant.

19. The method of claim 1 wherein said therapeutic composition is an anorectic.

20. The method of claim 1 wherein said therapeutic composition is an analgesic.

21. A therapeutic composition adapted to prevent drug overdosage and adapted for oral administration in addition to therapeutic ingredients having psychoactive characteristics comprising a coating on the surface of said therapeutic composition, said coating including between about 0.25 to 2.0 mg. of an emetic chemical comprising a major proportion of methyl cephaeline and cephaeline, and a minor proportion of psychotrine, O-methylpsychotrine and emetamine.

22. The therapeutic composition of claim 21 wherein said therapeutic composition is an antihistamine selected from the group consisting of dimenhydrinate, pseudo-ephedrine, trimeprazine, quasaifenesin, chlorpheniramine, phenylpropanolamine and caramiphen, chlorpheniramine and phenylpropanolamine, Ornade, promethazine HCI, phenylpropanolamine, pheniramine, pyrilamine, Pyribenzamine, tri-methobenzamide, diphenhydramine, chlorpheniramine, and mixtures thereof.

23. The therapeutic composition of claim 21 wherein said therapeutic composition is selected from the group consisting of perphenazine and amitriptylline, perphenazine and amitriptylline, Triavil, and mixtures thereof.

24. The therapeutic composition of claim 21 wherein said therapeutic composition is an analgesic selected from the group consisting of narcotics, pentazocine HCI, acetylsalicylic acid, butalbital, phenacetin, ASA, and caffiene, propoxyphene, propoxyphene napsylate, chlorpheniramine and ASA, acetaminophen, and mixtures thereof.

25. The therapeutic composition of claim 24 wherein said narcotics is selected from the group consisting of dolophin, meperedine, oxycodone, hydromorphine HCI, codiene, and mixtures thereof.

26. The therapeutic composition of claim 21 wherein said therapeutic composition is a muscle relaxant selected from the group consisting of orphenadrine citrate, chlorzoxazene, carisoprodol, methocarbomol, phenylbutazone, and mixtures thereof.

27. The therapeutic composition of claim 21 additionally including an opaque coating means surrounding said emetic chemical.

28. The therapeutic composition of claim 21 wherein said emetic chemical comprises between about 40% wt. and 85% wt. of methyl cephaeline, between about 10% wt. and 40% wt. of cephaeline, between about 2% wt. and 12% wt. of psychotrine, between about 1% wt. and 6% wt. of O-methylpsychotrine, and between about 1% wt. and 6% wt. of emetamine.

29. The therapeutic composition of claim 28 wherein said emetic chemical additionally includes between about 1% wt. and 6% wt. of ipecamine and between about 1% wt. and 6% wt. of hydro-ipecamine.

30. The therapeutic composition of claim 29 wherein said emetic chemical additionally includes between about 1% wt. and 6% wt. of ipecacuanhic acid.

31. The therapeutic composition of claim 30 wherein said emetic chemical additionally includes between about 1% wt. and 6% wt. of emetine hydrochloride.

32. The therapeutic composition of claim 21 wherein said therapeutic composition is a neuroleptic drug selected from the group consisting of phenothiazines, thioxanthines, butyrophenones, rauwolfia compounds, benzoquinolizine, phenylpiperazine, acridan, indolic derivatives, loxapine, and mixtures thereof.

33. The therapeutic composition of claim 32 wherein said phenothiazines is selected from the group consisting of chlorpromazine, thioridiazine, trifluooperazine, fluphenazine, promazine, triflupromazine, mesoridazine, piperacetazine, acetophenazine, butaperazine, carphenazine, perphenazine, prochlorperazine, thiopropazine, thioproperazine, and mixtures thereof.

34. The therapeutic composition of claim 32 wherein said butyrophenones is selected from the group consisting of haloperidol, triperidal, and mixtures thereof.

35. The therapeutic composition of claim 32 wherein said rauwolfia compound is selected from the group consisting of rauwolfia, rauwolfia serpintina, and mixtures thereof.

36. The therapeutic composition of claim 32 wherein said benzoquinolizines is tetrabinazine.

37. The therapeutic composition of claim 32 wherein said phenylpiperazine is oxypertine.

38. The therapeutic composition of claim 32 wherein said indolic derivatives is molindone.

39. The therapeutic composition of claim 21 wherein said theropeutic composition is an anxiolytic-minor tranquilizer selected from the group consisting of benzodiazepines, diphenylmethanes, hydroxyzine, chlormezanone, meprobamate, and mixtures thereof.

40. The tharapuetic composition of claim 39 wherein said benzodiazepines is selected from the group consisting of diazepam, oxazepam, chlordiazepoxide, chlordiazepoxide and clidinium, and mixtures thereof.

41. The therapeutic composition of claim 39 wherein said hydroxyzine is selected from the group consisting of hydroxyzine, hydroxyzine pamoate, and mixtures thereof.

42. The therapeutic composition of claim 21 wherein said therapeutic composition of a sedative-hypnotic selected from the group consisting of barbiturates, glutethimide, fluazepam, methprylon, ethchlorynol, Promethazine, chloral-hydrate, methaqualone, and mixtures thereof.

43. The therapeutic composition of claim 42 wherein said barbiturates is selected from the group consisting of secobarbital sodium, phenobarbital, amobarbital, pentobarbital, pentobarbital and carbomel, mephobarbital, secobarbital and amobarbital, butabarbital, and mixtures thereof.

44. The therapeutic composition of claim 21 wherein said therapeutic composition is lithium carbonate.

45. The therapeutic composition of claim 21 wherein said therapeutic composition is methylphenidate.

46. The therapeutic composition of claim 21 wherein said therapeutic composition is an anticonvulsant selected from the group consisting of phengtoin, sodium, mephenytoin, paramethadione, trimethadione, and mixtures thereof.

47. The therapeutic composition of claim 21 wherein said therapeutic composition is an antiparkinson selected from the group consisting of trihexyphenidyl, procyclidine HCI, benztropine, and mixtures thereof.

48. The therapeutic composition of claim 21 wherein said therapeutic composition is an antidepressant selected from the group consisting of tricyclics, doxepin, MAO inhibitors, protriptyline HCI, and mixtures thereof.

49. The therapeutic composition of claim 48 wherein said tricyclics is selected from the group consisting of amitriptyline, imipramine, nortriptyline HCI, desipramine HCI, and mixtures thereof.

50. The therapeutic composition of claim 48 wherein said MAO inhibitors is selected from the group consisting of tranylcypromine, isocarboxazid, nialamid, phenelzine, and mixtures thereof.

51. The therapeutic composition of claim 21 wherein said therapeutic composition is an anorexic selected from the group consisting of amphetamines, non-amphetamines, and mixtures thereof.

52. The therapeutic composition of claim 51 wherein said amphetamines is selected from the group consisting of amphetamine sulfate, dextro amphetamine, levo amphetamine, methamphetamine HIC, and mixtures thereof.

53. The therapeutic composition of claim 51 wherein said non-amphetamines is selected from the group consisting of phentermine resin, diethylproprion, phenmetazine HCI, mazindol, and mixtures thereof.

* * * * *